United States Patent [19]

Puskas et al.

[11] Patent Number: 4,467,111

[45] Date of Patent: Aug. 21, 1984

[54] PROCESS FOR PURIFICATION OF CRUDE TEREPHTHALIC ACID

[75] Inventors: Imre Puskas, Glen Ellyn; David E. James, Batavia, both of Ill.

[73] Assignee: Standard Oil Company (Indiana), Chicago, Ill.

[21] Appl. No.: 515,796

[22] Filed: Jul. 21, 1983

Related U.S. Application Data

[62] Division of Ser. No. 316,337, Oct. 29, 1981, Pat. No. 4,421,676.

[51] Int. Cl.$^3$ .............................................. C07C 51/42
[52] U.S. Cl. .................................... 562/487; 502/185; 502/230; 562/485
[58] Field of Search ................ 562/485, 489; 502/185, 502/230

[56] References Cited

U.S. PATENT DOCUMENTS

| | | | |
|---|---|---|---|
| 3,265,729 | 8/1966 | Olsen et al. | 562/487 |
| 3,522,298 | 7/1970 | Bryant et al. | 562/487 |
| 3,542,863 | 11/1970 | Zimonerschied | 562/487 |
| 3,546,285 | 12/1970 | Witt | 562/487 |
| 3,584,039 | 6/1971 | Meyer | 562/487 X |
| 3,591,629 | 7/1971 | Stancell et al. | 562/487 |
| 3,607,921 | 9/1971 | Stancell et al. | 562/487 |
| 3,726,915 | 4/1973 | Pohlmann | 562/487 |
| 3,799,976 | 3/1974 | Nienburg et al. | 562/487 |
| 4,260,817 | 4/1981 | Thompson et al. | 562/487 |

Primary Examiner—Natalie Trousof
Assistant Examiner—Vera C. Clarke
Attorney, Agent, or Firm—William C. Clarke; William T. McClain; William H. Magidson

[57] ABSTRACT

A catalyst and process for purifying crude terephthalic acid wherein the catalyst is prepared by contacting a carbonaceous support with an aqueous solution of sodium tetranitropalladate.

6 Claims, No Drawings

PROCESS FOR PURIFICATION OF CRUDE TEREPHTHALIC ACID

This is a division of application Ser. No. 316,337, filed Oct. 29, 1981, now U.S. Pat. No. 4,421,676.

BACKGROUND OF THE INVENTION

Purifiction of crude terephthalic acid by hydrogenation over a suitable catalyst is well-known. Hydrogenation offers the easiest route for removal of 4-carboxybenzaldehyde (4-CBA) impurity from the crude terephthalic acid (TA). This invention is directed to an improved process for the hydrogenation of crude terephthalic acid in the presence of a catalyst prepared by utilizing palladium metal deposited upon an active carbon support from soluble palladium complexes which react with the carbon to produce a catalyst of improved activity and/or selectivity in hydrogenating 4-carboxybenzaldehyde.

Catalysts comprising a Group VIII metal upon an inert carrier are known for use in various hydrogenation reactions. They are usually prepared by impregnating a support material with a solution of a compound of a Group VIII metal and reducing the impregnated compound to the metal. Catalyst improvements typically have been directed to obtaining increased hydrogenation activity rather than increased activity and/or selectivity in hydrogenating specific compounds.

It is an object of the instant invention to provide an improved method for preparing a supported catalyst of a Group VIII metal. A particular object is to provide a method for preparing such catalysts having increased catalytic activity and/or selectivity in the reduction of 4-carboxybenzaldehyde. Another object is to provide a catalyst composition which comprises crystallites of catalytically active palladium upon the surface of a porous carbonaceous support material wherein a catalyst of improved activity and/or selectivity is obtained for use in a process for reduction of 4-carboxybenzaldehyde in purification of crude terephthalic acid containing up to 10,000 ppm of 4-carboxybenzyaldehyde. Still further objects will be apparent from the following specification.

The field of this invention accordingly relates to Group VIII metal catalysts for hydrogenation and purification of terephthalic acid suitable for polyester polymers and copolymers useful in the manufacture of textile fibers. These polymers and copolymers have been made by condensing terephthalic acid with ethylene glycol and other dihydric alcohols.

As with other supported catalysts, the activity and selectivity of a Group VIII metal catalyst upon a carrier depends on numerous factors such as the amount of Group VIII metal or metals present in the catalyst, the type of support, the method by which the Group VIII metal is deposited and the distribution of the metal on the support.

Such Group VIII catalysts are limited in their ability to selectivity hydrogenate impurities in the terephthalic acid, especially 4-carboxybenzaldehyde. Users of terephthalic acid, such as textile fiber manufacturers, often put a rigorous limitation on the allowable concentration of 4-carboxybenzaldehyde in terephthalic acid.

Typically, Group VIII metal catalysts, such as palladium catalysts, are prepared by causing a palladium salt to be adsorbed from a solution onto a carrier. In one procedure as is taught in U.S. Pat. No. 2,857,337, the salt is then treated with a water-soluble metal hydroxide or basic carbonate which is thereafter reduced to metallic palladium by reducing agents such as formaldehyde, glucose, hydrazine, glycerine and the like. Other conventional methods of preparing palladium catalysts have been taught. U.S. Pat. No. 2,802,794 teaches impregnation of an activated alumina support material with a solution of a compound of the platinum metal group and reducing the impregnated compound to the metal. The preconditioned activated alumina is obtained by heating a hydrated alumina to a temperature of up to 800° C. whereby a microporous alumina is obtained.

U.S. Pat. No. 3,138,560 to Keith, et al., teaches that when sodium tetrachloropalladate palladium chloride is added to many carbon supports, most of the palladium is immediately deposited as a shiny film of metallic palladium. Catalysts so prepared generally have low activities and it has been theorized that the palladium compound is directly reduced to palladium metal by the presence of functional groups, such as aldehydes or free electrons on the carbon surface. Palladium catalysts are taught accordingly as advantageously prepared by fixing the palladium as an insoluble compound prior to reduction to avoid the problems of migration and crystallite growth which can occur when a metal is reduced from solution. Keith, U.S. Pat. No. 3,138,560 teaches inclusion of an oxidizing agent, such as hydrogen peroxide to hydrolyze the palladium prior to reduction by the carbon, thus obtaining improved palladium dispersion and a highly active catalyst. U.S. Pat. No. 3,288,725 to Aftandilian teaches that catalysts produced by deposition of a transition metal compound upon an inert particulate solid and subsequent reduction often have a disadvantage in that uniform deposition of the transition metal compound upon the surface of the inert particulate is accomplished with great difficulty. Hence, when the metal compound is reduced, the metal atoms deposited on the surface thereof are not exposed, are therefore not completely reduced and maximum potential catalytic activity is not achieved. Aftandilian, U.S. Pat. No. 3,288,725 teaches that reaction of the metal compound with a particulate surface having a suitable hydroxyl group content, followed by reduction with a borohydride produces an improved catalyst. U.S. Pat. No. 3,737,395 to Arnold, et al., teaches a process for preparing a catalyst which avoids formation of gels which cause lower activity. The catalysts are taught as having uniform and controlled deposition of palladium or platinum and a metallic promoter onto particulate carbon. An aqueous slurry is formed of the palladium or platinum compound and the water soluble metallic promoter. A precipitant is then added to precipitate the palladium or platinum and the metallic promoter, followed by coreduction of both with a mild reducing agent such as formaldehyde, hydrazine, sodium formate, glucose or hydrogen. U.S. Pat. No. 3,271,327 to McEvoy, et al., teaches a process for depositing palladium upon the surface of a nonporous support material wherein the palladium forms a thin, firm and adherent coating, thus obtaining maximum catalytic activity by means of a thin, peripheral distribution of palladium oxide in the support material. U.S. Pat. No. 3,328,465 to Spiegler teaches the preparation of palladium metal deposited on nonporous carbon support admixed with a porous carbon. The resulting catalyst is taught as resulting in a rate of hydrogenation about twice that of a hydrogenation process using the same amount of palladium deposited on a nonporous carbon. Previously, carbon used for support of palladium had been mainly porous carbon of vegetable or animal origin. Due to the high porosity of the carbon, some of the palladium became trapped in the pores and did not contribute to the activity of the catalyst. Another disadvantage was that such porous catalysts became fouled with the products of hydrogenation. By dilution of the nonporous carbon with porous carbon, the catalyst metal is distributed throughout the entire carbon without plugging the pores of the porous carbon.

The impurities in crude terephthalic acid prepared from para-xylene are partially oxidized products such as toluic acid and 4-carboxybenzaldehyde. These impurities usually are present in significant amounts. Toluic acid is not a particularly harmful impurity, in that it is readily removed by cooling and crystallizing terephthalic acid solutions containing it. Other impurities, and particularly 4-carboxybenzaldehyde, are more difficult to remove from terephthalic acid as such. Purification of crude terephthalic acid containing a high concentration of 4-carboxybenzaldehyde (4-CBA) is usually accomplished by converting 4-CBA by hydrogenation over a suitable catalyst to products which can be easily separated from the terephthalic acid by crystallization. However, only with great difficulty can the level of 4-CBA be reduced to levels below the limitation required by textile manufacturers. 4-Carboxybenzaldehyde is a particularly undesirable impurity because it acts as a chain-stopper during polyesterification of terephthalic acid.

Accordingly, a catalyst and process are highly desirable whereby impurities in crude terephthalic acid such as 4-carboxybenzaldehyde are hydrogenated to very low levels by selective reduction to readily separable compounds.

A number of techniques and processes have been developed to purify terephthalic acid by hydrogenation using palladium or platinum catalysts conventionally prepared as described above. Various devices are utilized to obtain the desired selectivity and activity in hydrogenating 4-carboxybenzaldehyde.

U.S. Pat. No. 3,522,298 to Bryant, et al., teaches a process wherein crude terephthalic acid is admixed with an inert gaseous carrier such as steam. The vapor mixture is contacted at a temperature of from 600° to 1000° F. with hydrogen in the presence of a catalyst such as a Group VIII metal upon a carbonaceous support, i.e., palladium upon powdered carbon. Vaporized terephthalic acid is separated by condensation from other constituents in the vapor, e.g., steam, other impurities. U.S. Pat. No. 3,542,863 to Zimmerschied teaches that hot formic acid treatment of a palladium metal on charcoal catalyst controls the activity and/or reactivity in instances where initial activity of a fresh catalyst is excessive and causes over-hydrogenation of aromatic rings or carboxylic acid groups or where catalysts have become deactivated due to use which oxygenated hydrocarbons. U.S. Pat. No. 3,584,039 to Meyer teaches purification of terephthalic acid by hydrogenation in aqueous liquid phase upon a Group VIII metal on carbon in the presence of hydrogen followed by crystallization from the mother liquor. U.S. Pat. No. 3,591,629 to Stancell, et al., teaches that a biphenyl treated catalyst of a Group VIII metal on activated carbon particles minimizes the conversion of terephthalic acid in the presence of hydrogen while effecting high conversions of 4-carboxybenzaldehyde contaminating the commercial acid. U.S. Pat. No. 3,607,921 to Stancell teaches that contact of crude terephthalic acid with carbon monoxide in the presence of palladium on carbon support effects a high percentage conversion of 4-carboxybenzaldehyde contaminating the acid. Surface area of the metal on the carbon support is taught as being extremely high, to 120 square meters per gram. U.S. Pat. No. 3,726,915 to Pohlmann teaches that copper based on palladium in palladium/carbon catalysts increases the activity of palladium/carbon catalysts in the hydrogenation of 4-carboxybenzaldehyde. U.S. Pat. No. 3,799,976 to Nienburg, et al., teaches purification of terephthalic acid containing 4-carboxybenzaldehyde by heating an aqueous mixture of the crude acid with formic acid in contact with a Group VIII metal as catalyst. U.S. Pat. No. 4,260,817 to Thompson, et al., teaches a method for purifying crude terephthalic acid by hydrogenating the crude acid to make toluic acid from 4-carboxybenzaldehyde and para-xylene from terephthalyl dialdehyde wherein the reduction takes place in two stages, the aldehyde radical forming an alcohol radical and in turn forming a methyl radical. The catalyst comprises two Group VIII metals on carbon particles.

Accordingly, it is well-known that crude terephthalic acid containing 4-carboxybenzaldehyde and other impurities can be purified by hydrogenation over a Group VIII metal or metals on carbon catalyst. However, more selective catalysts and processes are highly desirable wherein crude terephthalic acid containing high levels of 4-carboxybenzaldehyde is selectively hydrogenated to contain very low levels of 4-carboxybenzaldehyde.

SUMMARY

A catalyst and process for producing a purified terephthalic acid wherein 4-carboxybenzaldehyde is reduced to very low levels, to less than 100 parts per million in a standard laboratory evaluation, which comprises reacting in liquid phase a mixture of hydrogen and crude terephthalic acid in the presence of a catalyst compound comprising a palladium metal catalyst at a temperature of from about 100° C. to about 300° C. and a pressure from about 200 to about 1500 psi, wherein the catalyst compound is prepared by contacting a porous carbonaceous support with an aqueous solution of sodium tetranitritopalladate. The catalyst compound can be prepared in situ from sodium nitrite and palladium chloride.

DETAILED DESCRIPTION OF THE INVENTION

The catalyst and process of the instant invention relate to purification of terephthalic acid wherein 4-carboxybenzaldehyde (4-CBA) content is reduced to a low level, to less than 100 parts per million (ppm) in a standard laboratory test. The general method requires use of a palladium catalyst prepared by adsorbing palladium on a porous carbonaceous support having a surface area of at least 600 m$^2$/g from a nearly neutral aqueous solution of a precursor comprising a complex palladium salt. The complex salt is prepared by reacting a salt of palladium in aqueous solution with a soluble salt of nitrous acid. Depending on the stoichiometric quantities of the reagents, the following complexes or mixed ligand complexes can be present in solution: Na$_2$Pd(NO$_2$)$_4$, Na$_2$Pd(NO$_2$)$_3$Cl, Na$_2$Pd(NO$_2$)$_2$Cl$_2$ and Na$_2$Pd(NO$_2$)Cl$_3$.

The porous carbonaceous support or substrate is any suitable granular carbon having a surface area of at least 600 m²/g (N₂, BET method). Activated carbon granules of high surface area prepared from plant, animal or mineral sources can be used. While carbon granules are preferred, the method of this invention would also extend to carbon used in the form of pellets and other particulate forms. Preferably the substrate is activated carbon of plant or animal origin, most preferably of coconut charcoal.

It has been found that catalysts prepared by the above method are effective in purifying crude terephthalic acid. Moreover, the palladium on carbon catalyst is selective in reducing 4-carboxybenzaldehyde in the presence of hydrogen to low levels of less than 100 ppm under standard laboratory conditions.

The palladium catalyst of this invention is characterized by being prepared from salts of palladium in solutions of sodium nitrite wherein the sodium nitrite is present preferably in substantially stoichiometric quantities to give Na₂Pd(NO₂)₄ or mixed chloride-nitrite complexes. The palladium salt is adsorbed upon the surface of a porous carbonaceous support over a period of from 1 to 24 hours. Reduction to metallic palladium occurs. The resulting composition comprising the palladium on the support, i.e. activated carbon, is washed, filtered and dried. The catalyst can be used immediately for terephthalic acid purification. However, in a laboratory evaluation, a water slurry of the freshly-prepared catalyst is heated under hydrogen, for a period of about 1¾ to 2 hours at a temperature of 270° C. After the composition is cooled, the catalyst particles are filtered from the water slurry and dried under vacuum at approximately 80° C.

The catalyst of the process of the instant invention is believed to comprise palladium crystallites predominantly less than 35 Å in longitudinal measurement upon a support of carbonaceous material of plant origin, animal origin or mineral origin.

For reasons which are not understood, it has been found that preparation of a catalyst comprising palladium upon a carbonaceous material of activated carbon deposited from an aqueous solution of sodium tetranitritopalladate results in catalytically active palladium crystallites predominantly of less than 35 angstrom units (Å) in longitudinal measurement as measured by X-ray diffraction apparatus. Only crystallites with a longitudinal measurement larger than 35 Å can be detected due to the limit of resolution by the X-ray diffraction apparatus.

For reasons which are not understood, it has been found that hydrogenation of crude terephthalic acid with a catalyst comprising palladium metal deposited upon a porous activated carbon support prepared from an aqueous solution of sodium tetranitritopalladate purifies crude terephthalic acid very efficiently by reducing impurities of 4-carboxybenzaldehyde (4-CBA) to very low levels, as measured in a standard laboratory test.

The palladium salt utilized in the present invention is normally a palladium halide such as palladium chloride, palladium bromide, or palladium iodide. The halide slowly dissolves in water containing salts of nitrous acid such as sodium nitrite.

It has been found that to use sodium nitrite in a ratio of approximately 4 moles of sodium nitrite to 1 mole of palladium halide, such as palladium chloride, in preparation of the instant catalyst results in a hydrogenation catalyst which reduces 4-CBA content of crude terephthalic acid to a very low level, below 100 ppm in a standard laboratory test.

Surface area of supported metallic palladium can be calculated from X-ray diffraction data.

Alternatively, the surface area of the palladium metal deposited on active carbon can be calculated from carbon monoxide adsorption measurements. Palladium surface area of fresh catalysts of the present invention can be as high as 490 m²/g palladium, or even higher, as determined by either method.

The present invention provides a method of preparing supported metallic palladium whose crystallites are predominantly less than 35 Å in longitudinal measurement. This method consists of adsorbing and depositing palladium upon solid supporting granules of porous carbonaceous material such as activated charcoal from an aqueous solution of sodium tetranitritopalladate.

Palladium content of the carbon granules using the method of preparing the instant catalyst is usually less than 1.0 (wt) % of total catalyst weight, preferably less than 0.60 (wt) % of total catalyst weight. Higher concentrations of palladium can be deposited but apparently are of little avail because in the process of reducing 4-CBA levels in crude terephthalic acid, lower concentrations of palladium metal provide an efficient catalyst.

In an example of the preparation of the instant invented catalyst, granular activated vegetable charcoal is washed to remove charcoal fines. The washed vegetable charcoal is covered with water, the water layer is agitated, and slowly (dropwise) a solution of sodium tetranitritopalladate in water is introduced. The resulting mixture is kept under agitation at a temperature of from 0° C. to 100° C., preferably about 20° C. for a period of from 1 to 3 hours. The resulting catalyst particles are filtered from the mixture, washed with water at a temperature of from 0° to 50° C. and dried under vacuum of 100 mm Hg and 80° C. for a period of up to 16 hours.

To standardize the catalyst evaluation and to avoid measurement of a possibly misleading initial catalyst activity, the catalyst was treated with hydrogen at a temperature of 270° C. The catalyst particles were added to water in an autoclave and hydrogen gas under pressure was introduced into the autoclave. The mixture of catalyst particles, hydrogen gas and water was heated to a temperature of 270° C. for a period of about 1¾ to 2 hours. The mixture was then cooled. The catalyst was recovered and dried under vacuum.

The activity and selectivity of each catalyst were evaluated thereupon under standard laboratory conditions which simulate purification of terephthalic acid from the 4-carboxybenzaldehyde impurity under full-scale plant process conditions. 4-Carboxybenzaldehyde content of a terephthalic acid plant process steam can vary widely. Standard laboratory test conditions accordingly were used to measure activity and selectivity of catalyst compositions of the instant invention.

In summary, the instant invention comprises a method of preparing a catalyst composition, the catalyst composition prepared thereby and a catalytic hydrogenation process for hydrogenating crude terephthalic acid containing up to 10,000 ppm of 4-carboxybenzaldehyde in the presence of the catalyst composition, water, and hydrogen at a temperature of from about 100° C. to about 300° C. and a pressure of from about 200 to about 1500 psig, and recovering purified terephthalic acid from the treated mixture. The catalyst is prepared by contacting porous carbonaceous support granules with an aqueous solution of a tetranitritopalladate salt, the palladium content resulting on said granules being not greater than 0.6 (wt) percent and the palladium crystallites discernible by X-ray diffraction upon the surface of said granules being predominantly less than 35 Å in longitudinal measurement. The palladium tetranitritopalladate is prepared by reacting a nitrite salt with a palladium halide. Sodium nitrite and palladium chloride in stoichiometric quantities are preferred reagents to form complexes or mixed ligand complexes of the following: $Na_2Pd(NO_2)_4$, $Na_2Pd(NO_2)_3Cl$, $Na_2Pd(NO_2)_2Cl_2$ and $Na_2Pd(NO_2)Cl_3$.

The invention will be further illustrated by reference to the following specific examples.

EXAMPLE I

A number of catalysts were prepared to illustrate the present invention. In all cases approximately 4 to 8 mesh granular carbon of coconut shell origin was washed with distilled water to remove fines and then drained. The carbon was contacted with the solution of the palladium as indicated below, washed drained and dried at a temperature of approximately 80° C.

Catalyst A.

Granular coconut charcoal (18 g) was washed with distilled water to remove the carbon fines. The water was decanted and the moist charcoal was transferred into a 3-necked 300 ml flask. Distilled water (60 ml) was placed over it. A glass stirrer was installed which had a small paddle immersed into the water layer above the carbon. The stirrer was turned on. Palladium chloride (0.153 g) and 0.238 g sodium nitrite dissolved in distilled water (36.0 ml) were introduced. The $PdCl_2$ and $NaNO_2$ generated $Na_2Pd(NO_2)_4$ in situ. This solution was added dropwise from a dropping funnel to the stirred charcoal-water mixture. The stirring was continued for 2 hours. Then the catalyst was filtered, washed with hot water and dried in vacuum at 80° C. The catalyst, 17.5 g, had a 0.53 (wt) % Pd content.

Catalyst B.

In the method of Catalyst A, Catalyst B was prepared from $PdCl_2$, sodium nitrite as follows: $PdCl_2$ (0.153 g), water (36.0 ml), $NaNO_2$ (0.061 g) to prepare $PdCl_2 \cdot NaNO_2$.

Catalyst C.

In the method of Catalyst A, Catalyst C was prepared from $PdCl_2$, sodium nitrite as follows: $PdCl_2$ (0.154 g), water (36.0 ml), sodium nitrite (0.120 g), to prepare $PdCl_2 \cdot 2Na_2NO_2$.

Catalyst D.

In the method of Catalyst A, Catalyst D was prepared from $PdCl_2$ and sodium nitrite as follows: $PdCl_2$ (0.154 g), water (36.0 ml), sodium nitrite (0.300 g) to prepare $PdCl_2 \cdot 4NaNO_2$ containing excess of sodium nitrite.

Catalyst E.

In the method of Catalyst A, Catalyst E was prepared from $Pd(NO_3)_2$ and nitric acid as follows: $Pd(NO_3)_2$ (0.234 g), nitric acid (3.0 ml), water (36.0 ml) to prepare $Pd(NO_3)_2$ in 0.45N $HNO_3$. Stirring was continued for 17 hours. The catalyst, 17.8 g, had a 0.53 (wt) % Pd content.

Catalyst F.

In the procedure of Catalyst E, Catalyst F was prepared as follows: $Pd(NO_3)_2$ (0.234 g), $Al(NO_3)_3 \cdot 9H_2O$ (0.54 g) nitric acid (3.0 ml), water (36.0 ml) to prepare $Pd(NO_3)_2 \cdot Al(NO_3)_3$ in 0.45N $HNO_3$. The catalyst had a 0.49 (wt) % Pd content.

Before evaluating these catalysts, they were subjected to the following hydrogen treatment, as part of a regular laboratory evaluation procedure.

Distilled water (150 ml), the catalyst (6.0 g) and hydrogen gas at 200 psig were charged into a 300 ml rocking autoclave, heated to 270° C. and held at the temperature for 1¾ hours. After cooling, the catalyst was recovered and dried in vacuum oven at 80° C.

The above catalysts were evaluated for terephthalic acid (TA) purification. Catalyst and crude terephthalic acid were charged into a 300 ml rocking autoclave as follows: 12.9 g of crude TA, containing 7900 ppm 4-carboxybenzaldehyde (4-CBA); 150 ml distilled water; 0.17 g of catalyst under evaluation and 200 psig hydrogen gas. The reactor was heated to 250° C. and held at that temperature for 3½ hours. After cooling, the TA crystals were filtered, washed with 100 ml distilled water and dried in vacuo at 105° C. The purified TA was analyzed by liquid chromatography and by polargraphy. Results are in Table I. A commercially available palladium/carbon catalyst was hydrogenated and evaluated as were the catalysts of the instant invention.

TABLE I

| Catalyst Run No. | Description Of Palladium Precursor | 4-CBA (ppm) | (wt) % Pd | Pd Content >35Å %[a] | Pd Surface Area $M^2/g$[a] |
|---|---|---|---|---|---|
| Commercial 4761-85-1 | Unknown (Conventional) | 153 | 0.50 | 68 | 0.54 |
| A | | | | | |
| 5054-18-1 | $PdCl_2 \cdot$ | 39 | 0.53 | 0 | 1.26 |
| 5054-144-1 | $4NaNO_2$ | 80 | 0.49 | 11 | 1.05 |
| B | | | | | |
| 5293-48-1 | $PdCl_2 \cdot$ $NaNO_2$ | 380 | [b] | — | — |
| C | | | | | |
| 5293-47-1 | $PdCl_2 \cdot$ $2NaNO_2$ | 241 | [b] | — | — |
| D | | | | | |
| 5293-49-1 | $PdCl_2 \cdot$ $4NaNO_2$ Plus excess $NaNO_2$ | 240 | [b] | — | — |
| E | | | | | |
| 5054-16-1 | $PdNO_3$ | 311 | 0.53 | 25 | — |
| F | | | | | |
| 5054-35-1 | $PdNO_3$ | 261 | 0.49 | 21 | — |

[a]Measurements after hydrogen treatment at 270° C. Before hydrogen treatment, the palladium surface area is much higher. The size of the palladium crystallites usually increased during the hydrogen treatment at 270° C.
[b]Estimated 0.5 (wt) %.

What is claimed is:

1. A process for purifying crude terephthalic acid containing up to 10,000 ppm of 4-carboxybenzaldehyde wherein 4-carboxybenzaldehyde content is reduced to a level of less than 100 parts per million in a standard laboratory test wherein said process comprises hydrogenating said crude acid in liquid phase at a temperature of from about 100° C. to about 300° C. and a pressure of from about 200 to about 1500 psi with hydrogen in the presence of water and of a catalyst composition which comprises crystallites of catalytically active palladium upon the surface of a porous activated carbon support material having a surface area of at least 600 $m^2/g$ wherein said crystallites are predominantly less than 35 Å in longitudinal measurement, and wherein said catalyst composition is prepared by contacting said support with an aqueous solution of a nitritopalladate salt.

2. The process of claim 1 wherein said nitritopalladate salt is prepared by reacting stoichiometric quantities of a nitrite salt with a palladium halide selected from the group consisting of palladium chloride, palladium bromide and palladium iodide.

3. The process of claim 2 wherein said nitrite salt is sodium nitrite.

4. The process of claim 1 wherein said support material is selected from the group consisting of plant origin carbon, animal origin carbon, and mineral origin carbon.

5. The process of claim 4 wherein said plant origin carbon is coconut charcoal.

6. The process of claim 1 wherein said temperature is 250° C., and pressure of hydrogen is 200 psi.

* * * * *